(12) United States Patent
Buysse et al.

(10) Patent No.: US 6,352,536 B1
(45) Date of Patent: Mar. 5, 2002

(54) BIPOLAR ELECTROSURGICAL INSTRUMENT FOR SEALING VESSELS

(75) Inventors: Steven Paul Buysse, Longmont; Dale Francis Schmaltz, Fort Collins; Robert Luzzi, Boulder; Kirk Bryan Olson, Golden; Kate Ryland Lawes, Superior; Daniel Lee Trimberger, II, Greeley; Mathew Erle Mitchell; Jenifer Serafin Kennedy, both of Boulder, all of CO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/502,933

(22) Filed: Feb. 11, 2000

(51) Int. Cl.[7] ............................................... A61B 18/18
(52) U.S. Cl. ............................. 606/51; 30/342; 606/49
(58) Field of Search ..................... 606/48–52, 205–209, 606/33, 40; 81/416; 30/340, 342, 344

(56) References Cited

U.S. PATENT DOCUMENTS

| 2,305,156 A | * | 12/1942 | Grubel | |
| 3,643,663 A |   | 2/1972  | Sutter | |
| 5,019,092 A | * | 5/1991  | Klintmalm | 606/207 |
| 5,951,549 A |   | 9/1999  | Richardson et al. | |
| 6,050,996 A | * | 4/2000  | Schmaltz et al. | 606/51 |
| 6,203,877 B1 | * | 3/2001 | Kese et al. | 606/48 |

FOREIGN PATENT DOCUMENTS

| EP | 0 584 787 A1 | 3/1994 |
| EP | 0 853 922 A1 | 7/1998 |

* cited by examiner

Primary Examiner—Roy Gibson

(57) ABSTRACT

A bipolar electrosurgical instrument has opposable seal surfaces on its jaws for grasping and sealing vessels and vascular tissue. Inner and outer instrument members allow arcuate motion of the seal surfaces. An open lockbox provides a pivot with lateral support to maintain alignment of the lateral surfaces. Ratchets on the instrument members hold a constant closure force on the tissue during the seal process. A shank portion on each member is tuned to provide an appropriate spring force to hold the seal surfaces together. During surgery, the instrument can be used to grasp and clamp vascular tissue and apply bipolar electrosurgical current through the clamped tissue. In one embodiment, the seal surfaces are partially insulated to prevent a short circuit when the instrument jaws are closed together. In another embodiment, the seal surfaces are removably mounted on the jaws.

12 Claims, 5 Drawing Sheets

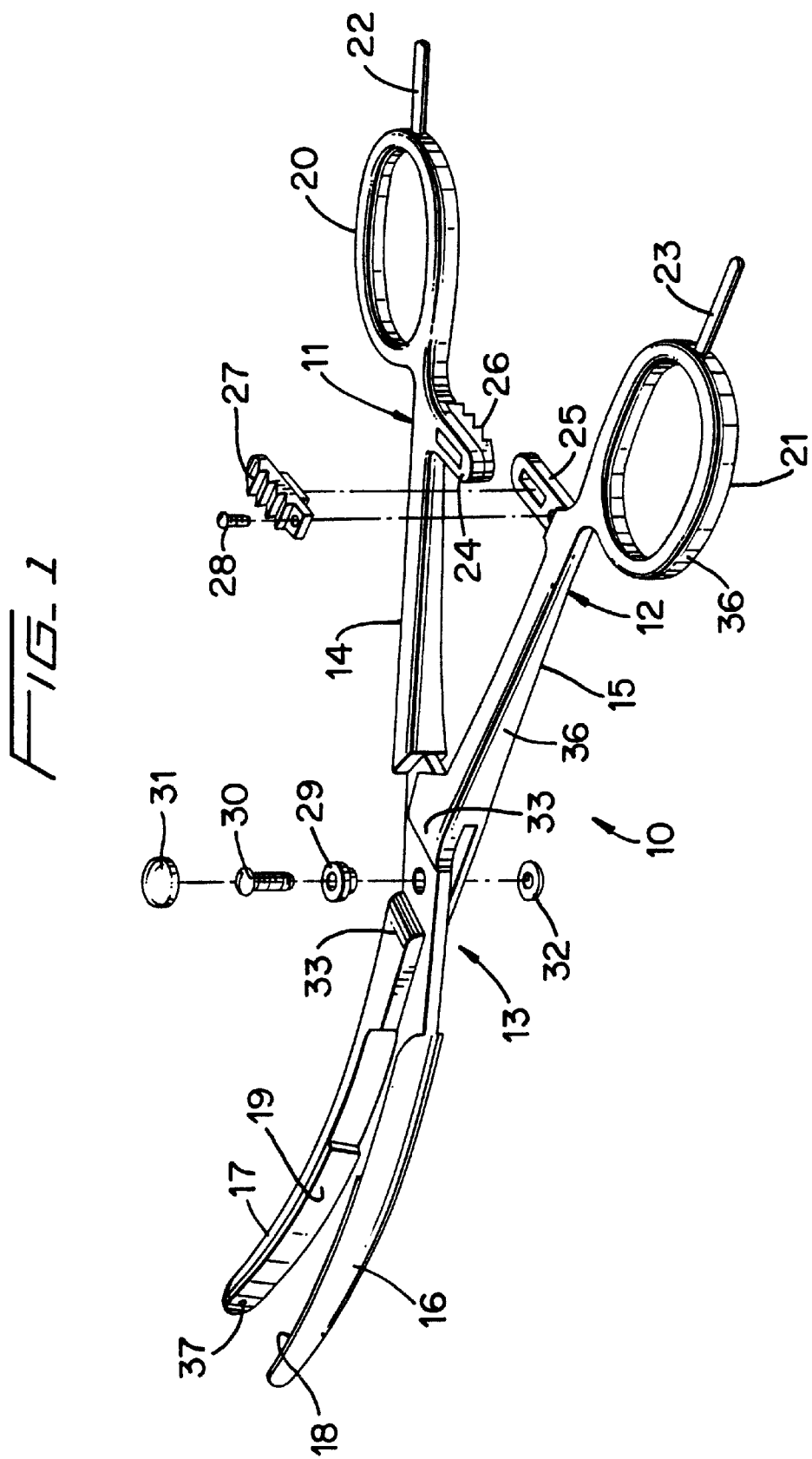

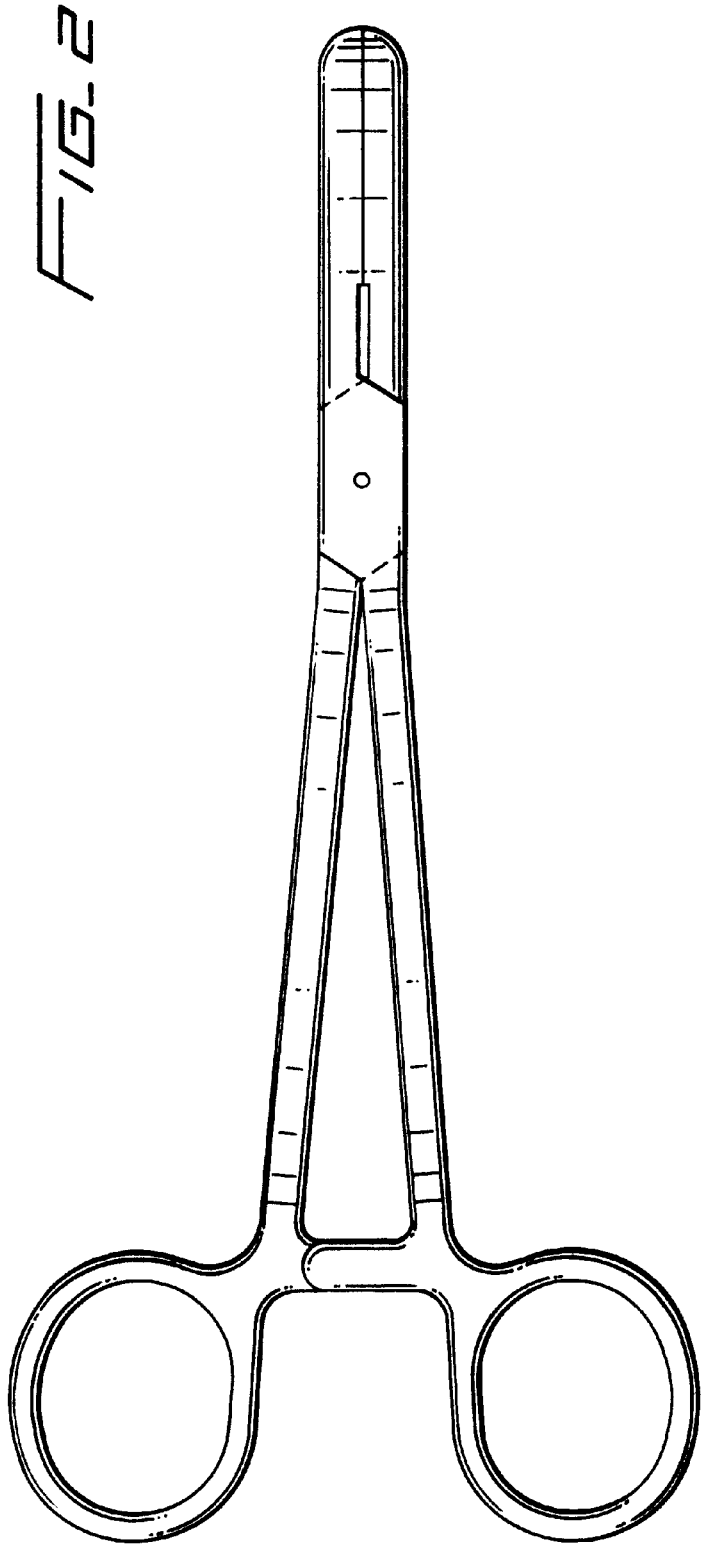
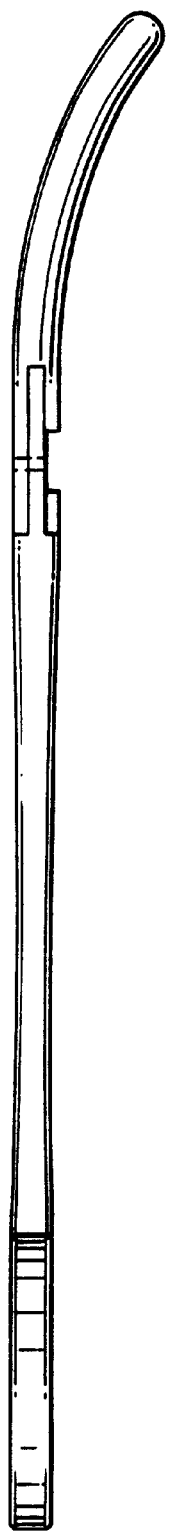

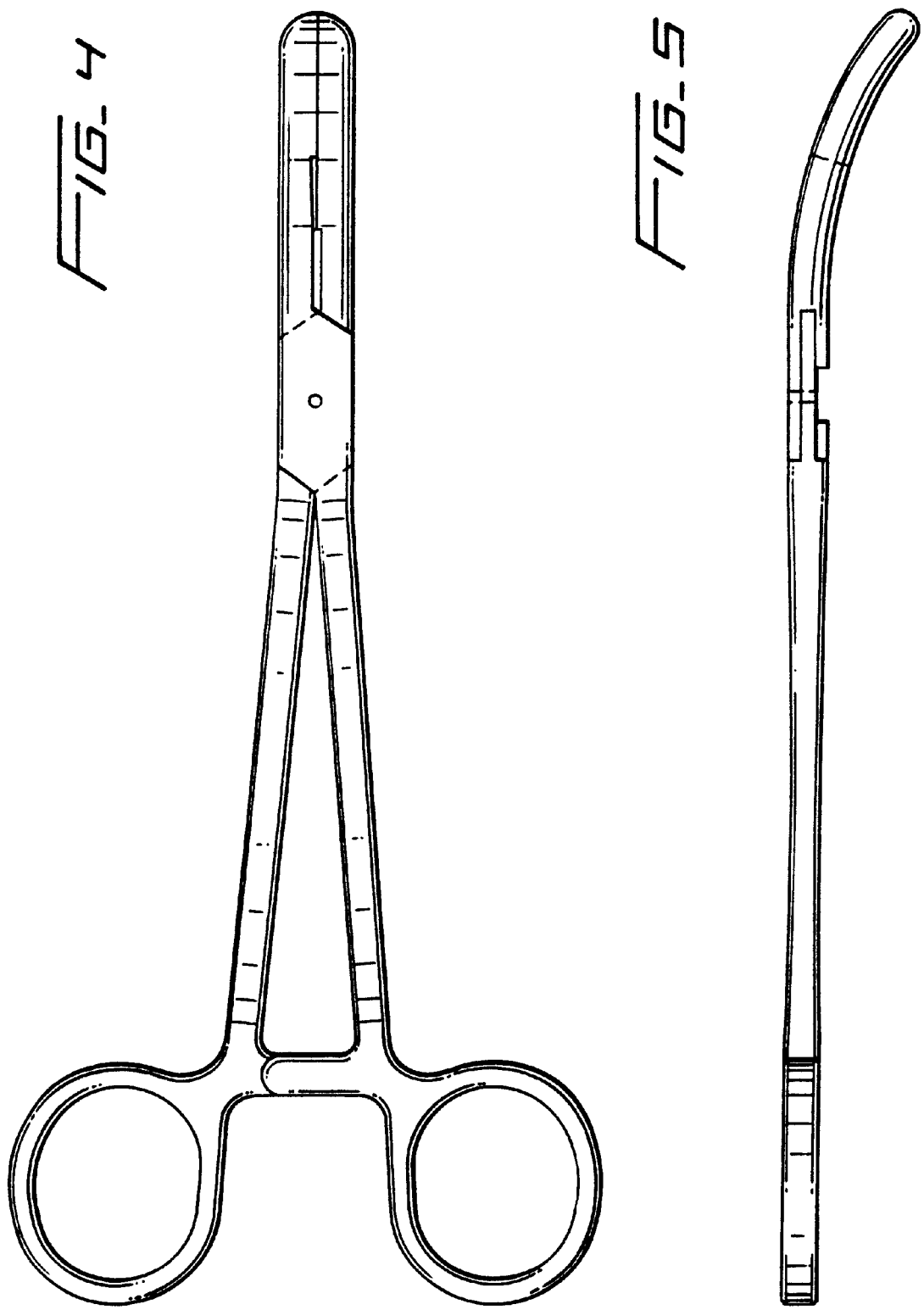

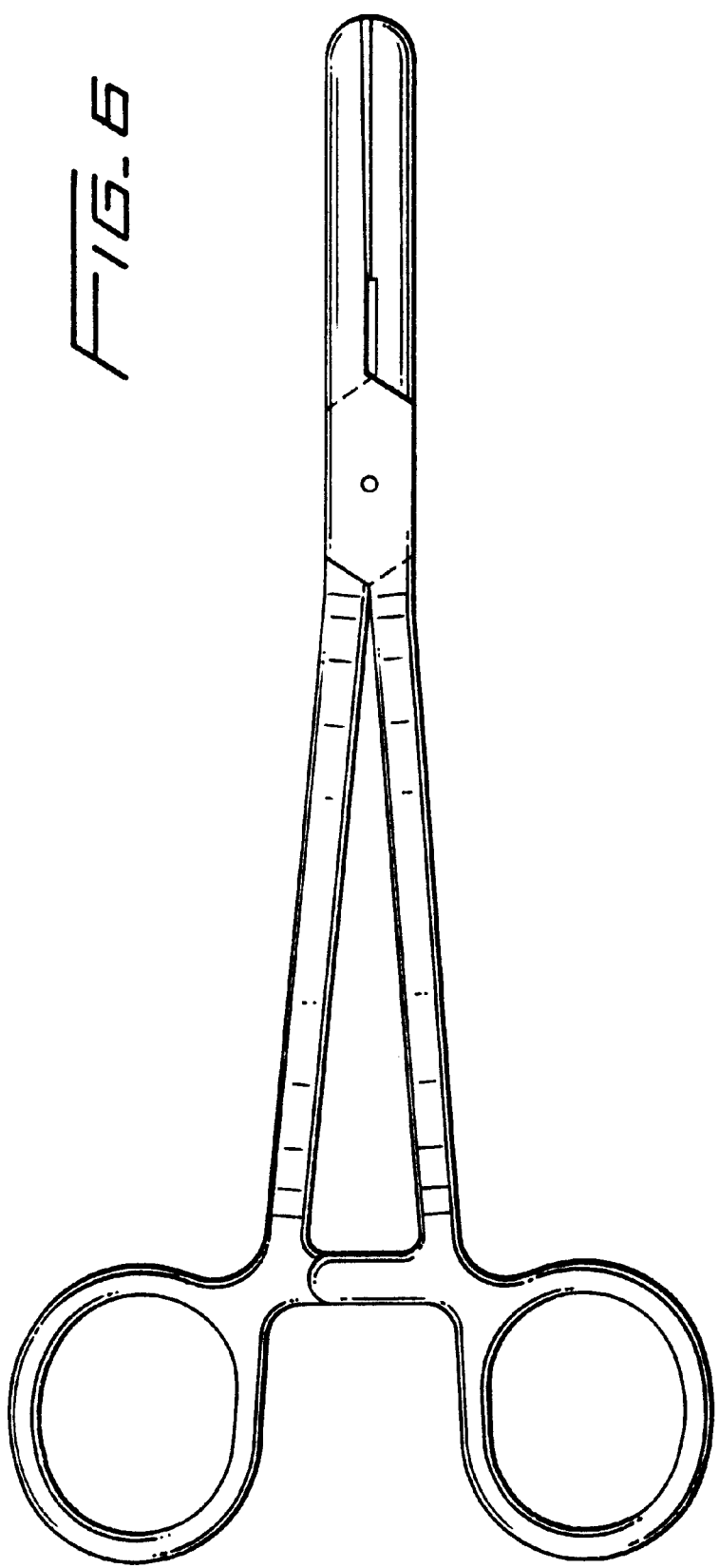

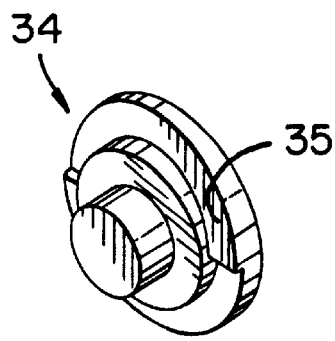
FIG_8
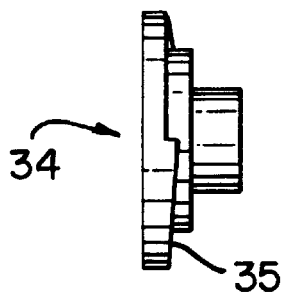
FIG_9
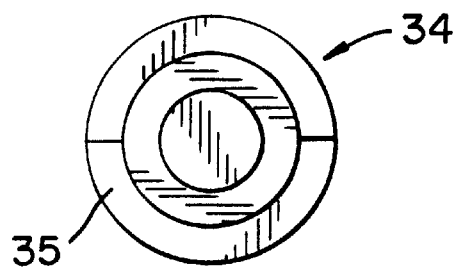
FIG_10
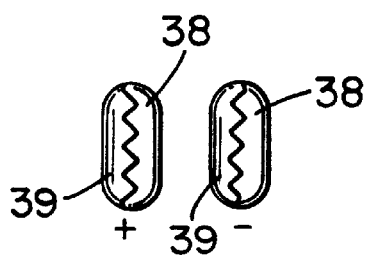
FIG_11A
FIG_11B

BIPOLAR ELECTROSURGICAL INSTRUMENT FOR SEALING VESSELS

FIELD OF THE INVENTION

This invention relates to an electrosurgical instrument for permanently closing vessels in a human or animal, and more particularly to a bipolar electrosurgical instrument that seals vessels and vascular tissue by applying a combination of pressure and electrosurgical current.

BACKGROUND OF THE DISCLOSURE

A hemostat is commonly used in surgical procedures to grasp, dissect and clamp tissue. It is typically a simple pliers-like tool that uses mechanical action between its jaws to constrict vessels without cutting them. It is also typical for hemostats to have an interlocking ratchet between the handles so that the device can be clamped and locked in place.

Many hemostats are used in a typical open-surgical procedure. Once vascular tissue has been clamped with a hemostat, it is common for a surgeon to tie a suture around the tissue to close it off permanently prior to removing the hemostat. Several hemostats may be left in the surgical field until the surgeon has the opportunity to tie a suture around each section of clamped tissue.

Small blood vessels have been closed using electrosurgical instruments without the need for sutures. For example, neurosurgeons have used bipolar instruments to coagulate vessels in the brain that are smaller than two millimeters in diameter. These bipolar instruments are typically tweezer-like devices with two arms that can be deflected toward each other to grasp tissue. However, it has been found that these instruments are not capable of sealing blood vessels with diameters larger than about two millimeters. There has been a long-felt need for an easy way to seal larger vessels and vascular tissue bundles without the need for sutures.

It is thought that the process of coagulating small vessels is fundamentally different than vessel sealing. Coagulation is defined as a process of desiccating tissue wherein the tissue cells are ruptured and dried. Vessel sealing is defined as the process of liquefying the collagen in the tissue so that it crosslinks and reforms into a fused mass. Thus, coagulation of small vessels is sufficient to permanently close them. Larger vessels need to be sealed to assure permanent closure.

A number of bipolar electrosurgical forceps and clamps are known in the field. However, these instruments are not designed to apply the correct pressure to a blood vessel to achieve a lasting seal. All of these instrument also suffer from the drawback that they do not combine the simplicity and familiarity of a hemostat with a bipolar electrosurgical circuit.

An example of a bipolar electrosurgical power curve for vessel sealing is disclosed in a U.S. patent application entitled, "Energy Delivery System for Vessel Sealing," Ser. No. 08/530,495, filed Sept. 19, 1995, and is hereby incorporated by reference and made a part of this disclosure.

A U.S. patent application entitled, "Vascular Tissue Sealing Pressure Control and Method," Ser. No. 08/530,450, filed on Sep. 19, 1995, discloses another surgical tool for sealing vessels, and is hereby incorporated by reference and made a part of this disclosure.

U.S. Pat. No. 371,664 discloses a pair of electric forceps with positive and negative electric poles located on the jaws.

U.S. Pat. No. 728,883 discloses an electrothemic instrument in which electricity is used to heat one of the jaws of the instrument.

U.S. Pat. No. 1,586,645 discloses a bipolar instrument for coagulating tissue.

U.S. Pat. No. 2,002,594 discloses a bipolar laparoscopic instrument for treating tissue, whereby coagulation and cutting of tissue can be performed with the same instrument.

U.S. Pat. No. 2,176,479 discloses an instrument for finding and removing metal particles. The jaws of the instrument are designed to complete an electrical circuit when conductive material is placed therebetween. An insulated pivot and an insulated ratchet are used to prevent a short circuit.

U.S. Pat. No. 3,651,811 discloses a bipolar electrosurgical instrument for cutting and coagulating tissue.

U.S. Pat. No. 4,005,714 discloses bipolar coagulation forceps with jaws that open and close by way of an actuating sleeve.

U.S. Pat. Nos. 4,370,980 and 5,116,332 disclose an electrocautery hemostats wherein the hemostatic clamping function and the electrocautery function may be accomplished with a single instrument. Monopolar electrosurgical designs are shown and described.

U.S. Pat. No. 4,552,143 discloses a family of removable switch electrocautery instruments, including an electrocautery hemostat. Monopolar electrosurgical designs are shown and described.

U.S. Pat. No. 5,026,370 discloses an electrocautery forceps instrument having an enclosed electrical switching mechanism. Monopolar electrosurgical designs are shown and described.

U.S. Pat. No. 5,443,463 discloses coagulating forceps having a plurality of electrodes.

U.S. Pat. No. 5,484,436 discloses bipolar electrosurgical instruments for simultaneously cutting and coagulating tissue.

The article, "The Mechanism of Blood Vessel Closure by High Frequency Electrocoagulation" discloses experiments upon the blood vessels of dogs. The sentence starting on the last line of page 823 describes "an electrode forceps, each of the blades being insulated form the other and each connected to a terminal of the high frequency generator."

The article, "Studies on coagulation and development bipolar coagulator" discloses on page 150 that, "It was not possible to coagulate safely arteries with a diameter larger than 2 to 2.5 mm." On page 151, line 5, it is noted that "Veins can be coagulated safely up to a diameter of 3 to 4 mm."

Russian Patent 401,367 discloses a bipolar instrument with a linkage that brings the working jaws together in a parallel manner.

Prior disclosures have not provided a design for a bipolar electrosurgical instrument capable of conveniently applying a constant pressure, from a calibrated spring-loaded source held by a ratchet, that is sufficient to seal vessels and vascular tissue.

SUMMARY OF THE INVENTION

It is the general objective of this invention to provide a bipolar electrosurgical instrument that can fuse tissue without the need for a suture or surgical clips. The instrument conducts electrosurgical current between two seal surfaces located on opposable jaws. The electrosurgical current passes through tissue clamped between the jaws and remolds the collagen to fuse the tissue and form a permanent seal.

One advantage of the invention is that blood vessels can be quickly fused and permanently sealed against passage of blood or other fluids. The instrument thereby reduces operating-room time, provides improved access to target tissues, and increases the efficiency of the surgical procedure.

Another advantage is that no sutures or staples are required to permanently seal blood vessels, and no foreign material is left in the body of the patient.

Yet another advantage is that vessels can be sealed as the instrument is applied, and then the instrument can be removed from the surgical field. This keeps the surgical field clear of extraneous tools that may hinder the surgeon's access to the surgical site.

Yet another advantage is that the proper amount of pressure can be applied by the instrument to the vessel or vessels, thereby increasing the likelihood of a successful surgical outcome.

The bipolar electrosurgical instrument of the present invention comprises inner and outer members connected by an open lockbox, interlocking ratchet teeth, and electrical terminals with conductive pathways leading to seal surfaces. The inner and outer members each have a ring handle near a proximal end and an opposable seal surface near a distal end. The proximal end is held and controlled by the surgeon, while the distal end is used to manipulate tissue. The open lockbox joins the inner and outer members to allow arcuate motion of each opposable seal surface. The open lockbox is generally designed to provide lateral support so that both seal surfaces move in approximately the same plane. The seal surfaces are preferably aligned opposite each other when the instrument jaws are closed together. To provide lateral support, the open lockbox comprises a pivot and at least one flange extending over the inner member and attached to the outer member.

The instrument is tuned to provide a proper closure force by adjusting the dimensions of a shank portion on each of the inner and outer members. The shank portion is defined as the portion of each member bounded by its respective ratchet stub and the open lockbox. During use, the surgeon squeezes the ring handles to compress tissue between the seal surfaces. The shank portion of each member flexes in the manner of a cantilever spring, and can be locked in a deflected position with the ratchet to hold a constant force. It is one of the objects of the invention to provide a range of ratchet stops that correspond to a range of appropriate closure forces on the seal surfaces of the instrument.

Ratchet teeth are located on each member near the ring handle. The ratchet teeth are generally designed to interlock against the spring force from the shanks. The spring force is thus transmitted through the pivot to hold the seal surfaces against each other. A range of closure forces is required in an instrument, depending on the type and thickness of the tissue to be sealed. It is thus desirable to have several ratchet stops, each providing a progressively larger force to the seal surfaces.

An electrical connector is located on each ring handle. The electrical connector may be a metal post that is integrally formed with the member and ring handle. Bipolar electrical cables from an electrosurgical generator are connected to the instrument at the electrical connectors. An electrically conductive path on each of the inner and outer members conducts the electrosurgical current to the seal surfaces. The electrically conductive path may be along the stainless steel members. An electrically insulative coating is preferably bonded to the outer surfaces of the members to protect the surgeon and patient against inadvertent electrical burns.

The following terms are herein defined as follows. The applied force of the instrument is the total force being applied to the tissue between the jaws. The jaws are the members near the distal end of the instrument, from the lockbox to the tip of the instrument. The electrodes are the metal surfaces that conduct electricity to the tissue. The seal surface is the feature on the electrode that comes in direct contact with the tissue. The shank is the portion of each member between the lockbox and the ratchet. The ring handles are the elements on the members, near the proximal end of the instrument, that are grasped by the surgeon. The lockbox is the structure that allows the members to pivot, including the pivot pin and other cooperating surfaces. The inner member is the member that is generally captured in the interior of the lockbox. The outer member is the member that is on the outside of the lockbox. Electrode pressure is calculated by dividing the applied force over the complete area of the seal surface. Tissue pressure is calculated by dividing the applied force over the area of tissue placed between the jaws.

It has been found through experimentation that an instrument for vessel fusion (also referred herein as vessel seing) should compress the tissue with a proper amount of pressure between the instrument jaws. The pressure is preferably sufficient to close any blood-carrying lumen. The pressure is preferably low enough so that the tissue is not split apart within the instrument jaws.

The jaws of the instrument should not short-circuit during the procedure. The tissue will typically decrease in thickness when electrosurgical current is applied, thereby allowing the seal surfaces to move closer together. This decrease in thickness should not result in the electrodes making direct contact with each other. Otherwise, a short circuit could give the electrosurgical current a preferential path around the tissue and may result in a poor seal.

BRIEF DESCRIPTION OF THE DRAWINGS

FIG. 1 is a perspective view of a bipolar instrument for vessel fusion, shown partially exploded.

FIG. 2 is a schematic plan view of a bipolar instrument for vessel fusion having a longer curved jaw.

FIG. 3 is a side view of the instrument shown in FIG. 2.

FIG. 4 is a schematic plan view of an alternative embodiment of an instrument for vessel fusion having a shorter curved jaw.

FIG. 5 is side view of the instrument shown in FIG. 4.

FIG. 6 is a schematic plan view of an alternative embodiment of an instrument for vessel fusion having a straight jaw.

FIG. 7 is a side view of the instrument shown in FIG. 7.

FIG. 8 is a perspective view of a shoulder pin.

FIG. 9 is a side view of a shoulder pin.

FIG. 10 is a front view of a shoulder pin.

FIG. 11 is a top view each of a pair of seal surfaces showing conductive regions and insulative regions that prevent a short circuit when the seal surfaces are mated in opposition.

DETAILED DESCRIPTION OF THE INVENTION

Referring to FIG. 1, the instrument 10 has an inner member 11 and an outer member 12. The members 11 and 12 are connected through an open lockbox 13 which has a gap between flanges 33. The terms "inner" and "outer" are used to distinguish the members 11 and 12, and their component parts, according to the members' respective positions at the open lockbox 13. The inner member 11 is fitted generally within the inner surfaces of the open lockbox 13 and is captured by the flanges 33. The outer member generally forms the outside surfaces of the open lockbox 13.

The inner member 11 has an inner shank 14, an inner jaw 16, and an inner ring handle 20. Similarly, the outer member 12 has an outer shank 15, an outer jaw 17, and an outer ring handle 21. The ring handles, 20 and 21, are designed for a surgeon to hold and manipulate the instrument 10. The jaws, 16 and 17, are designed to grasp tissue between the opposing seal surfaces 18 and 19.

Each shank, 14 and 15, has a respective ratchet stub 24 or 25. Ratchet teeth, 26 and 27, are designed to interlock in a manner that hold the members, 11 and 12, in position. The shanks 14 and 15 are deflected in the manner of a cantilever spring when the jaws are forced together by the surgeon. The deflection of the shanks 14 and 15 produces a spring restoring force that can be opposed by interlocking the ratchet teeth, 26 and 27.

The instrument 10 does not cause a short circuit when the ratchet teeth, 26 and 27, are interlocked. This is accomplished by a suitable selection and placement of electrically insulating materials. In the preferred embodiment, the ratchet teeth 26 and 27 are composed of a polymeric material which is press-fit into the ratchet stubs 24 and 25. A ratchet screw 28 is used in the preferred embodiment to secure the ratchet teeth 26 and 27 into the ratchet stubs 24 and 25. During manufacture, the ratchet teeth 26 and 27 may be formed from a blank after the blank has been press fit into the ratchet stubs 24 and 25.

In a second embodiment, one of the members, 11 or 12, includes the ratchet stub and ratchet teeth as in integral part of the member, while the other member, 12 or 11, has an insulative layer that prevents a short circuit between the members 11 and 12 when the ratchets are engaged.

The open lockbox 13 has the function of providing a pivoting joint for the members 11 and 12. In addition, the flanges 33 provide lateral support to help maintain alignment of the jaws 16 and 17. Closed lockbox designs are typically used in standard hemostat designs, wherein an inner member is completely captured through a slot in an outer member. The open lockbox 13 in present invention has a gap between the flanges 33 that is different from a closed lockbox design. The gap in the open lockbox 13 provides convenient access to install an electrically insulated pivot.

The electrically insulated pivot in the present invention comprises a shoulder washer 29 supporting a lockbox screw 30. The shoulder washer 29 is composed of an electrically insulative material that prevents a short circuit between the members 11 and 12. A large screw cap 31 fits over the head of the lockbox screw 30. A small screw cap 32 fits over the threaded end of the lockbox screw 30.

Each member 11 and 12 is connected to a pole of a bipolar electrosurgical generator. Electrical connectors 22 and 23 are located on the ring handles 20 and 21 to provide a convenient point of connection. The members 11 and 12 are formed of an electrically conductive material, such as stainless steel. The exposed surfaces of the members, except for the connectors 22 and 23 and the seal surfaces 18 and 19, are preferably spray coated with an insulating material.

The characteristics of the bipolar electrosurgical current are determined by the design of the electrosurgical generator. In the preferred embodiment, the generator will have an output wherein the peak-to-peak voltage will not exceed 130 Volts. This is because higher voltages can cause sparking which results in localized burning of tissue which may result in a failure of the tissue weld. The preferred embodiment has the generator capable of producing high frequency output current of at least 2 Amps RMS. High electrical current is important because it heats the tissue sufficiently to melt the collagen. Lower electrical currents will often produce weak tissue welds with low bursting strength.

During operation, the instrument 10 is used to grasp tissue between the seal surfaces 18 and 19. The surgeon squeezes the ring handles 20 and 21 together, causing pressure to be applied to the tissue. The ratchet teeth 26 and 27 are interlocked at the appropriate ratchet setting, depending on the tissue type and tissue thickness. Bipolar electrosurgical current is applied through the instrument and the tissue to cause the tissue to fuse.

The jaws 16 and 17 have a structure and cross-section that resist bending under load. Thus, for purposes of engineering analysis, the shank portions 14 and 15 act as a cantilever supported beam once the seal surfaces 18 and 19 have been mated. The length of this idealized cantilever beam extends from the lockbox screw 30 to the location of the respective ratchet subs 24 or 25. It is possible to model each shank as a cantilever spring having a spring constant. Each ratchet position is designed to transmit a particular closure force to the jaws 16 and 17 against the action of the restoring force of the cantilever spring.

The spring constant is generally a function of Young's Modulus of the shank material, the moment of inertia of the shank, and the length of the shank portion 14 and 15. When the jaws 16 and 17 of the instrument 10 are closed together, each shank 14 and 15 approximates a cantilever-supported beam. It is properly assumed that the deflection of each shank 14 and 15 remains within the linear range of its stress-strain curve. The behavior of such a beam is well known to materials engineers. A large spring constant will result in large closure forces between the seal surfaces 18 and 19. Similarly, a small spring constant will result in a small closure forces between the seal surfaces 18 and 19. The choice of a proper spring constant will depend on the length of the shank 14 or 15 and the distance between ratchet stops 26 and 27.

Experimental results in animal studies suggest that the magnitude of pressure exerted on the tissue by the seal surfaces 18 and 19 is important in assuring a proper surgical outcome. Tissue pressures within a working range of 7 $kg/cm^2$ to 13 $kg/cm^2$ have been shown to be effective for sealing arteries and vascular bundles. It is desirable to tune the spring constant of the shank portions 14 and 15, in conjunction with the placement of the ratchet teeth 26 and 27, such that successive ratchet positions will yield pressures within the working range. In one embodiment, the successive ratchet positions are two millimeters apart.

Pressure on the tissue can be described in several ways. Engineers will recognize that the amount of pressure exerted on the tissue depends on the surface area of the tissue that is in contact with the seal surfaces. In the one embodiment, the width of each seal surface 18 and 19 is in the range of 2 to 5 millimeters, and preferably 4 millimeters width, while the length of each seal surface 18 and 19 is preferably in the range of 10 to 30 millimeters. It has been found through experimentation that at least one interlocking ratchet position preferably holds the closure force between approximately 400 and 650 grams per millimeter of seal surface width. For example, if the width of the seal surface 18 and 19 is 4 millimeters, the closure force is preferably in the range of 1600 grams to 2600 grams. In one embodiment, the closure force is 525 grams per millimeter of width, yielding a closure force of 2100 grams for a 4 millimeter width seal surface 18 and 19.

It has been found experimentally that local current concentrations can result in an uneven tissue effect, and to reduce the possibility of this outcome, each seal surface 18 and 19 has a radiused edge in the preferred embodiment. In addition, a tapered seal surface 18 and 19 has been shown to be advantageous in certain embodiments because the taper allows for a relatively constant pressure on the tissue along the length of the seal surfaces 18 and 19. The width of the seal surfaces 18 and 19 is adjusted, in certain embodiments, wherein the closure force divided by the width is approximately constant along the length.

In one embodiment, a stop 37, made from insulative material, is located in the instrument to maintain a minimum separation of at least 0.3 millimeters between the seal surfaces 18 and 19, as shown in FIG. 1. The stop 37 reduces the possibility of short circuits between the seal surfaces 18 and 19.

In certain embodiments, as shown in FIG. 11, the seal surfaces 18 and 19 comprise conductive regions 38 and insulative regions 39 arranged such that each conductive region 38 opposes an insulative region 39 when the opposable seal surfaces 18 and 19 are mated in opposition. The seal surfaces 18 and 19, in certain embodiments, may be removable from its respective member 11 or 12 by standard mechanical interfaces, such as a pin and socket arrangement.

FIG. 2 shows an embodiment for a thirty-two millimeter curved seal surface. FIG. is a side view of FIG. 2. The members 11 and 12 in FIG. 2 are formed from, American Iron and Steel Institute 410 stainless steel. The length and cross sectional area of the shank portions 14 and 15 are shown in FIGS. 2 and 3 to provide a spring constant of twenty-five pounds per inch deflection.

The embodiment shown in FIGS. 4 and 5 has a twenty millimeter curved seal surface. The embodiment shown in FIGS. 6 and 7 has a thirty-two millimeter straight seal surface. Each embodiment in FIGS. 2 through 7 is designed to have the look and feel of a standard hemostat.

FIGS. 8, 9 and 10 show three views of a shoulder pin 34 that can be used, in certain embodiments, instead of the lockbox screw 30 to connect the members 11 and 12. The shoulder pin 34 has at least one ramp surface 35 that engages one of the members 11 or 12 to cause increasing mechanical interference as the jaws 16 and 17 move toward each other. In one embodiment, the shoulder pin 34 forms part of the open lockbox 13 to aid alignment of the seal surfaces 18 and 19. In another embodiment, the shoulder pin 34 is used without an open-lockbox 13, and movably pins the members 11 and 12 together without a flange 33. The interference fit may require the calibration of the instrument 10 to insure that the applied force will be sufficient to provide the appropriate working pressure between the seal surfaces 18 and 19. A slightly higher spring constant in the shank portions 14 and 15 is preferably used, depending on the level of interference caused by the shoulder pin.

A method of using the bipolar electrosurgical instrument comprises the following steps. A surgeon grasps the ring handles 20 and 21 on the instrument 10 to manipulate the jaws 16 and 17. A vessel or vascular tissue is compressed between the opposable seal surfaces 18 and 19. The opposable seal surfaces 18 and 19 preferably come together in aligned opposition due to the alignment action of the open-lockbox 13, or in certain embodiments due to the alignment action of the shoulder pin 34. The surgeon further deflects the shank portions 14 and 15 of the members 11 and 12 to engage the ratchet teeth 26 and 27. The engagement of the ratchet teeth 26 and 27 hold the shank portions 14 and 15 in their deflected positions to provide a constant spring force that is transmitted as a closure force to the jaws 16 and 17. An electrosurgical generator is connected to the instrument 10 through connectors 22 and 23 on the ring handles 20 and 21. An electrical switch is used to close a circuit between the generator and the instrument 10. The switch may be a footswitch such as Valleylab's catalog number E6009, available from Valleylab Inc., Boulder Colo. The electrosurgical current flows through an electrically conductive path on each of the inner and outer members 11 and 12 between its respective electrical connector, 22 or 23, and its respective seal surface, 18 or 19. An electrically insulative coating 36 substantially covers each member 11 and 12, except for the seal surfaces 18 and 19, to protect the surgeon against electrical arcs.

It is to be understood that the above described embodiments are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A method of using a bipolar electrosurgical instrument, the method comprising the following steps:

moving inner and outer members to grasp tissue between opposable seal surfaces, the inner and outer members each having a ring handle near a proximal end and an opposable seal surface near a distal end;

aligning the opposable seal surfaces in opposition using an open lockbox, the open lockbox joining the inner and outer members to allow arcuate motion of each opposable seal surface, the open lockbox comprising a pivot and at least one flange extending over the inner member and attached to the outer member;

engaging ratchet teeth located near each ring handle, the ratchet teeth providing at least one interlocking ratchet position that holds a closure force between the opposable seal surfaces;

deflecting a shank portion on each of the inner and outer members to create a spring load, the shank portion bounded by its respective ratchet teeth and the pivot;

connecting bipolar electrosurgical current to the instrument through an electrical connector located on each ring handle, such that the current flows through an electrically conductive path on each of the inner and outer members between its respective electrical connector and its respective seal surface to provide for electrosurgical current flow between the opposable seal surfaces, and wherein an electrically insulative coating substantially covers each ring handle, each shank portion, and the open lockbox.

2. A bipolar electrosurgical instrument comprising:

inner and outer members each including a distal end having an opposable seal surface disposed thereon;

one of the members having an open lockbox sufficiently dimensioned to at least partially receive the other of the members;

a pivot joining the inner and outer members and for allowing motion of each opposable seal surface relative to each another;

a ratchet disposed on one of said members having at least one complimentary interlocking ratchet disposed on the other of said members for holding a closure force between the opposable seal surfaces; and a stop disposed on one of the opposable seal surfaces for maintaining a minimum separation distance between the opposable seal surfaces.

3. A bipolar electrosurgical instrument according to claim 2 wherein said stop is made from an insulative material.

4. A bipolar electrosurgical instrument according to claim 2 wherein said pivot is made from an insulative material.

5. A bipolar electrosurgical instrument according to claim 2 wherein said pivot includes a shoulder pin having a ramp surface for varying the interference fit between the inner and outer members during arcuate motion of each opposable seal surface.

6. A bipolar electrosurgical instrument according to claim 2 wherein said opposable seal surfaces are removable from said distal ends of said inner and outer members.

7. A bipolar electrosurgical instrument according to claim 2 wherein said ratchet includes ratchet teeth which are removably engageable with said ratchet.

8. A bipolar electrosurgical instrument according to claim 7 wherein said ratchet teeth are made from an polymeric material.

9. A bipolar electrosurgical instrument according to claim 7 wherein said ratchet teeth engage said ratchet in a press-fit manner.

10. A bipolar electrosurgical instrument comprising:

inner and outer members each including a distal end having an opposable seal surface disposed thereon;

a shoulder pin made from an insulative material for joining the inner and outer members and for allowing motion of each opposable seal surface relative to each another, the shoulder pin having a ramp surface for varying the interference fit between the inner and outer members during relative motion of each opposable seal surface;

a ratchet disposed on one of said members having at least one complimentary interlocking ratchet disposed on the other of said members for holding a closure force between the opposable seal surfaces; and a stop disposed on one of the opposable seal surfaces for maintaining a minimum separation distance between the opposable seal surfaces.

11. A bipolar electrosurgical instrument according to claim 10 wherein said stop is made from an insulative material.

12. A bipolar electrosurgical instrument according to claim 10 wherein said opposable seal surfaces are removable from said distal ends of said inner and outer members.

* * * * *